(12) United States Patent
Claremon et al.

(10) Patent No.: US 6,350,744 B1
(45) Date of Patent: Feb. 26, 2002

(54) COMPOUNDS HAVING CYTOKINE INHIBITORY ACTIVITY

(75) Inventors: David A. Claremon, Maple Glen; Gerald S. Ponticello, Lansdale, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/433,247

(22) Filed: Nov. 4, 1999

Related U.S. Application Data

(60) Provisional application No. 60/109,306, filed on Nov. 20, 1998.

(51) Int. Cl.[7] .................. A61K 31/501; A61K 31/5377; C07D 401/14; C07D 403/14; C07D 413/14
(52) U.S. Cl. .............. 514/230.5; 514/252.03; 514/252.02; 514/256; 514/275; 514/255.05; 514/318; 514/334; 544/238; 544/295; 544/296; 544/405; 546/194; 546/257
(58) Field of Search ................. 544/238, 114; 514/252.02, 252.03, 236.5

(56) References Cited

U.S. PATENT DOCUMENTS 6,174,901 B1 * 1/2001 Mantlo et al. ............. 514/333

FOREIGN PATENT DOCUMENTS

| WO | WO 97/33883 | 9/1997 |
| WO | WO 98/24782 | 6/1998 |

OTHER PUBLICATIONS

OH, *Annals of The Academy of Medicine* 27p. 738–743 (Med Line Abstract), 1999.*
Livingston, *Journal Of Cellular Biochemistry*, 64 p 19–26, 1997.*
J.C. Lee et al., Nature, 372:739–746(1994).
C.A. Dinarello, Nutrition, 11:492–494 (1995).
C.A. Dinarello, Eur. Cytokine Netw., 5:517–531(1994).
C.A. Dinarello, Immunology, 4:133–145(1992).
B.J. Votta et al., Bone, 15:533–538(1994).
R.B. Kimble et al., Endocrinology, 136:3054–3061(1995).
R. Kitazawa et al., J.Clin. Invest., 94:2397–2406(1994).
H.M. Van Dullemen et al., Gastroenterology, 109:129–135(1995).
S.H. Murch et al., Bailiere's Clinical Gastroenterology, 8:133–148(1994).
A.D. Olson et al., J.Ped. Gastroenterology and Nutrition, 16:241–246(1993).
F.C. Breedveld et al., Brit. Medical Bull., 51:493–502(1995).
F.M. Brennan et al., Brit. Medical Bull., 51:368–384(1995).
M.J. Elliott et al., Bailliere's Clinical Gastroenterology, 9:633–652(1995).
M.J. Elliott et al., Lancet, 344:1105–1110(1994).
M.J. Elliott et al., Lancet, 344:1125–1127(1994).
C.A. Dinarello, Rev. Infect. Diseases, 6:51–95 (1984).
G. Poli, et al., Proc. Natl. Acad. Sci. USA, 87: 782–785 (1990).
J. Chin and M.J. Kostura, J. Immunology, 151:5574–5585 (1993).

* cited by examiner

*Primary Examiner*—Emily Bernhardt
(74) *Attorney, Agent, or Firm*—Shu Muk Lee; David L. Rose

(57) ABSTRACT

There are disclosed compounds of formula (I)

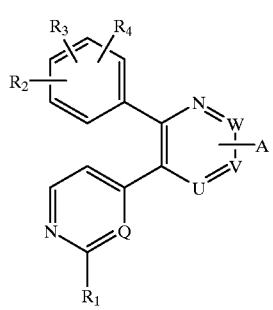

(I)

and pharmaceutically acceptable salts thereof which exhibit utility for the treatment of cytokine mediated diseases such as arthritis.

7 Claims, No Drawings

US 6,350,744 B1

COMPOUNDS HAVING CYTOKINE INHIBITORY ACTIVITY

This application claims the benefit of U.S. patent application Ser. No. 60/109,306, filed Nov. 20, 1998, now abandoned.

BACKGROUND OF THE INVENTION

The present invention relates to substituted heterocyclic compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells which are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. Dinarello et al., *Rev. Infect. Disease*, 6, 51 (1984). The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., *Proc. Natl. Acad. Sci.*, 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD 11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention relates to compound I of the formula

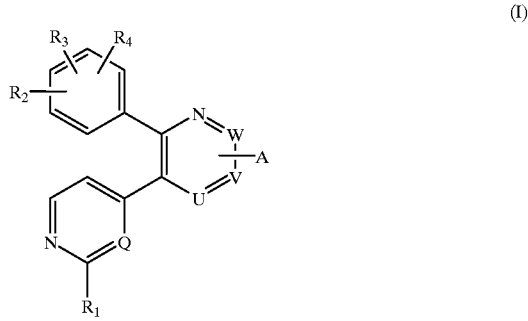

wherein:
A is hydrogen, or a saturated heterocyclic group selected from pyrrolidine, morpholine and piperidine; with the nitrogen atom or atoms optionally substituted with hydrogen or $C_1$–$C_6$ alkyl;
Q, U, V and W are independently CH or N;
$R^1$ is hydrogen or NH($C_1$–$C_6$ alkyl) aryl,
$R^2$, $R^3$ and $R^4$ independently represent a member selected from the group consisting of: hydrogen; halo; hydroxy; $CF_3$; $NH_2$; $NO_2$, $C_1$–$C_6$ alkyl, substituted $C_1$–$C_6$ alkyl; $C_1$–$C_6$ alkoxy, substituted $C_1$–$C_6$ alkoxy; $C_3$–$C_8$ cycloalkyl, substituted $C_3$–$C_8$ cycloalkyl; aryl or substituted aryl;
or a pharmaceutically acceptable addition salt and/or hydrate thereof, or where applicable, a geometric or optical isomer or racemic mixture thereof.

A pharmaceutical composition is also included in the invention described herein, which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

DETAILED DESCRIPTION OF THE INVENTION

The present invention relates to compound I of the formula

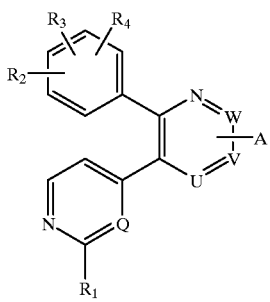
(I)

wherein:

A is hydrogen, or a saturated heterocyclic group selected from pyrrolidine, morpholine and piperidine, with the nitrogen atom or atoms optionally substituted with hydrogen or $C_1$–$C_6$ alkyl;

Q. U. V and W are independently CH or N;

$R^1$ is hydrogen or NH($C_1$–$C_6$ alkyl) aryl;

$R^2$, $R^3$ and $R^4$ independently represent a member selected from the group consisting of. hydrogen; halo; hydroxy $CF_3$; $NH_2$; $NO_2$, $C_1$–$C_6$ alkyl, substituted $C_1$–$C_6$ alkyl $C_1$–$C_6$ alkoxy, substituted $C_1$–$C_6$ alkoxy; $C_3$–$C_8$ cycloalkyl, substituted $C_3$–$C_8$ cycloalkyl; aryl or substituted aryl;

or a pharmaceutically acceptable addition salt and/or hydrate thereof, or where applicable, a geometric or optical isomer or racemic mixture thereof.

In a preferred embodiment, there are disclosed compounds of formula I wherein

A is hydrogen, or piperidine with the nitrogen atom substituted with hydrogen or $C_1$–$C_6$ alkyl;

Q, U and W are independently CH or N;

$R^1$ is hydrogen or NHCH($CH_3$) phenyl;

$R^2$, $R^3$ and $R^4$ are independently hydrogen or $CF_3$;

or a pharmaceutically acceptable addition salt and/or hydrate thereof, or where applicable, a geometric or optical isomer or racemic mixture thereof.

Representative species falling within the present invention include the following:

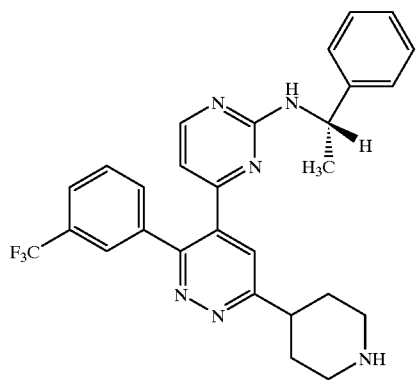

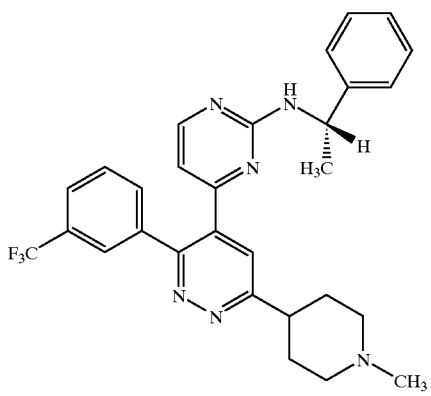

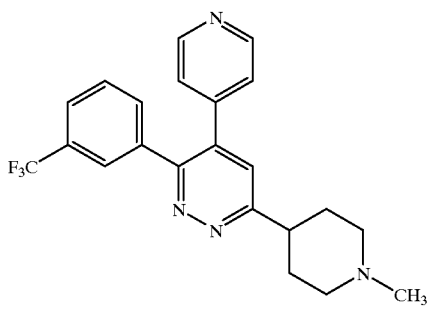

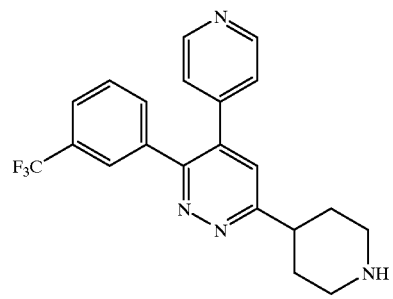

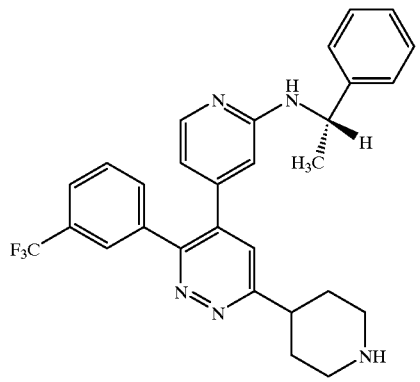

-continued

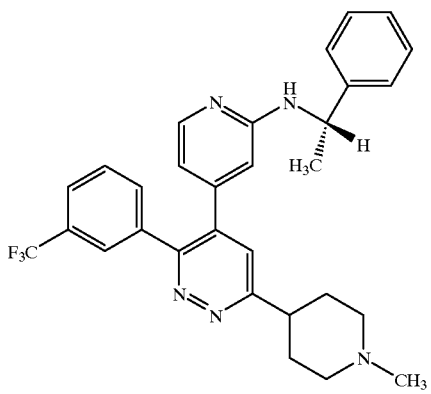

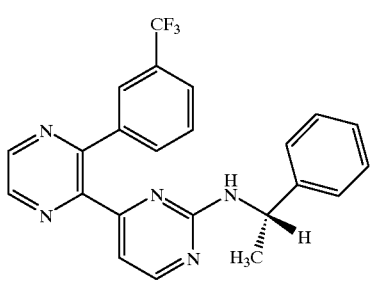

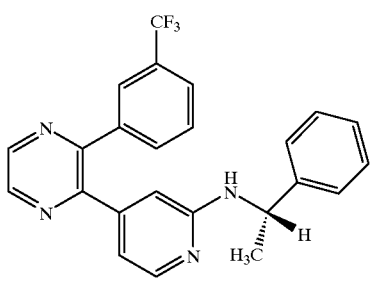

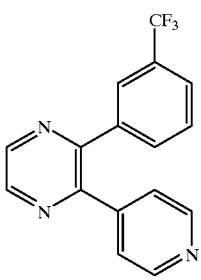

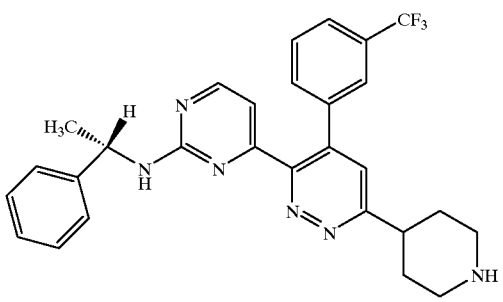

-continued

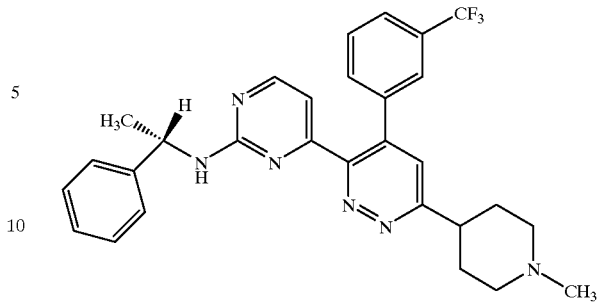

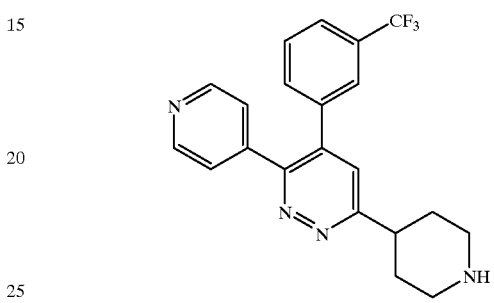

Unless otherwise stated or indicated, the following definitions shall apply throughout the specification and claims.

The term "alkyl" refers to a monovalent alkane (hydrocarbon) derived radical containing from 1 to 15 carbon atoms unless otherwise defined. It may be straight or branched, and when of sufficient size, e.g., C3–15 may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl. Alkyl also includes a straight or branched alkyl group The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "aryl" refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl or naphthyl substituted with one or two groups.

The terms "heterocycloalkyl" and "heterocyclyl" refer to a cycloalkyl group (nonaromatic) in which one of the carbon atoms in the ring is replaced by a heteroatom selected from O, S(O)y or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochenistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "TNF mediated disease or disease state" refers to disease states in which TNF plays a role, either by production or increased activity levels of TNF itself, or by causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppresive amount" is meant an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the invention are prepared by the following reaction schemes. All substituents are as defined above unless indicated otherwise.

Preparation of Pyridazines

Scheme I

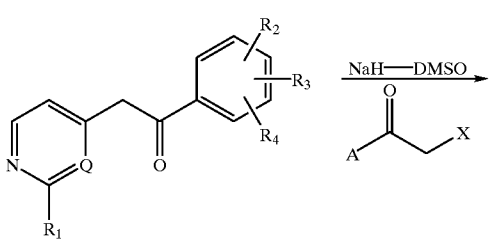

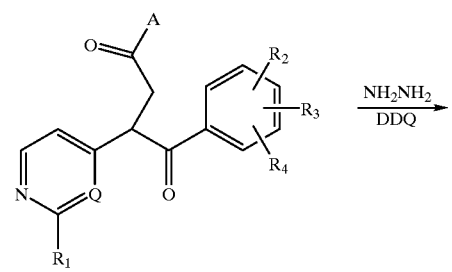

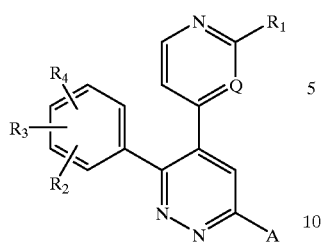

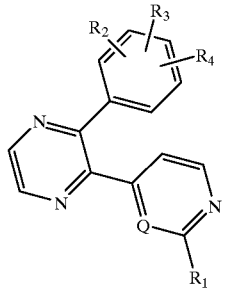

Scheme II

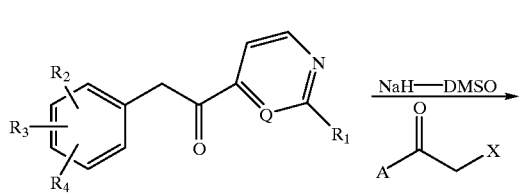

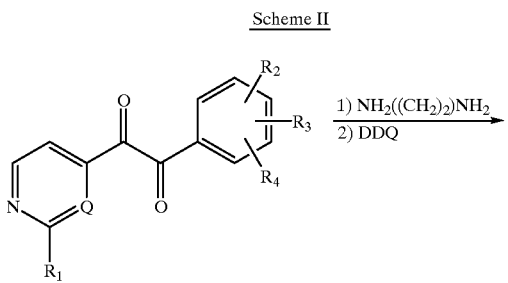

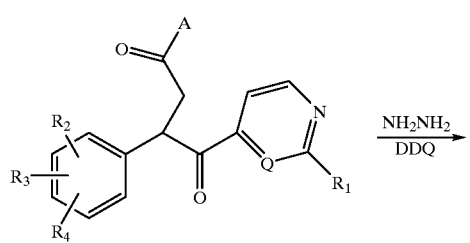

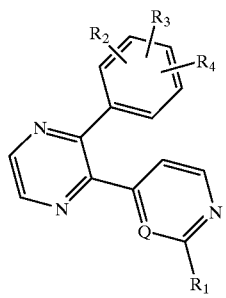

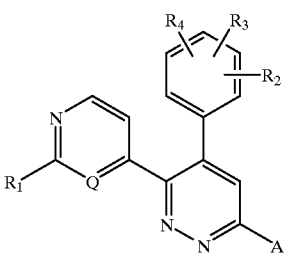

Preparation of Pyrazines

Scheme I

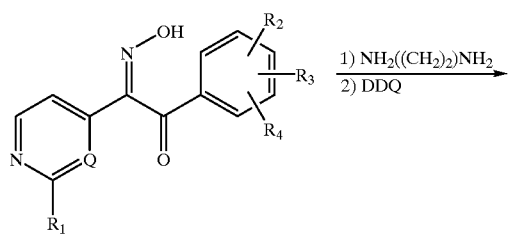

The compounds of formula 1 can be used in the prophylactic or therapeutic treatment of disease states in mammals which are exacerbated or caused by excessive or unregulated cytokines, e.g., IL-1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

EXAMPLE 1

α-(2-methylthiopyrimidine-4-yl)-3-trifluromethylacetophenone (3)

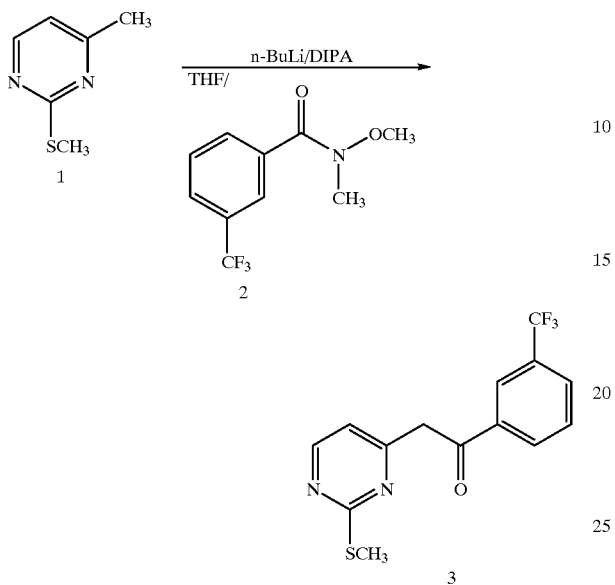

Under Ar, a solution of diisopropylamine (70 mL, 0.5 mol) in THF (500 mL) was cooled to −70° C. and a solution of 2.5 N n-BuLi in hexane (0.5 mol) was added dropwise. After addition, the solution was stirred for 0.5 hr at −70° C. and then a solution of 1 (44 g, 0.31 mol) in THF (25 mL) was added dropwise. After 0.75 hr, a solution of 2 (87.4 g, 0.38 mol) in THF (25 mL) was added dropwise. The reaction was stirred at −70° C. for an additional 2 hr and then treated with a saturated solution of aqueous NaHCO3. The aqueous layer was extracted with EtOAc (3×) and the combined organic extract was washed with brine, dried, filtered and concentrated to dryness to yield a solid. The solid was crystallized from methylene chloride-hexanes to yield 66g of impure product which was further triturated with 30% ether-hexanes to yield 45g of 3. Further chromatography of the mother liquors on a Still column (100 mm) and elution with 15% ethyl acetate-hexanes yielded another 32.6g to yield a total of 77.6g of 3.

EXAMPLE 2

4-(2-chloroacetyl)-N-carbobenzoxypiperidine: (5)

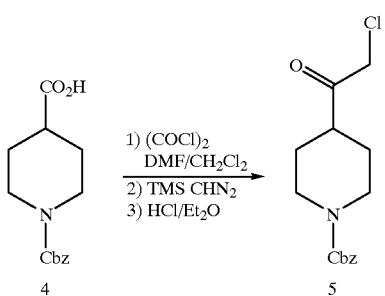

Under Ar, the acid 4 was dissolved in methylene chloride (500 mL) with DMF (0.5 mL) and the solution cooled to 0–4° C. Then oxalyl chloride (5.5 mL, 63 mmol) was added dropwise. After addition, the reaction was stirred at ambient temperature for 3 h, concentrated to dryness and the residue was treated with THF (100 mL) and acetonitrile (100 mL). The solution was cooled to 0–4° C. and a solution of 2.0M trimethylsilyldiazomethane in Et2O (25 mL, 50 mmol) was added dropwise. After addition, the reaction was stirred at 0–4° C. for 1 h and then at ambient temperature for 1 h. Then the solvent was removed under reduced pressure (20mm) and the residue was dissolved in Et$_2$O (200 mL), cooled to 0–4° C. and treated dropwise with 1.0M HCl in Et$_2$O mL, 50 mmol.) with N$_2$ evolution. After addition, the ice bath was removed and the reaction stirred at ambient temperature. After 15 h, a solution of saturated NaHCO$_3$ was added. The layers were separated and the aqueous layer was further extracted with EtOAc (2×). The combined organic extracts were dried, filtered and concentrated to dryness. The residue was chromatographed on a Still column (80 mm) and the product eluted with 20 EtOAc hexanes to yield 7.6 g of 5.

EXAMPLE 3

4-(3-trifluoromethylphenyl)-4-oxo-3-(2-methylthiopyrimidin-4-yl)-1-oxo-1-N-carbobenzoxypiperidin-4-yl) butane (6)

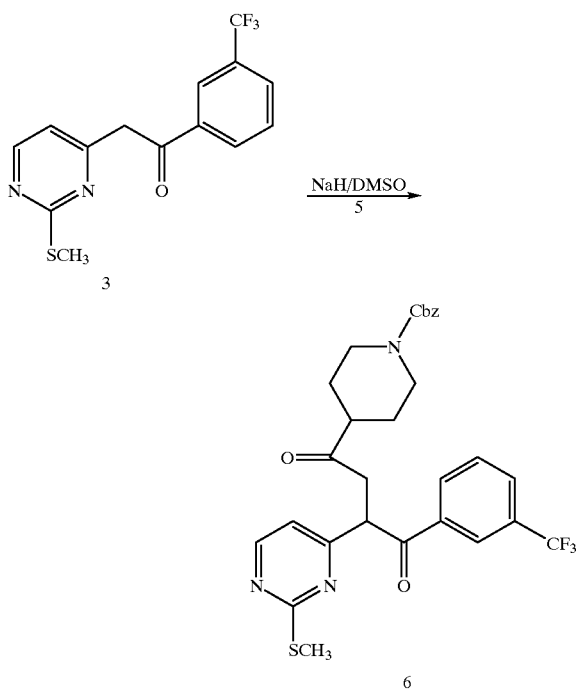

Under Ar, a solution of 3 (5.0 g, 16.0 mmol) in DMSO (30 mL) was added dropwise to a suspension of 95% NaH (0.42g, 17.6 mmol) in DMSO (20 mL) cooled in an ice bath. After 20 min., a solution of 5 (5.2 g, 17.6 mmol) in DMSO (20 mL) was added in a steady stream. After addition, the solution was stirred at ambient temperature. After 15 h, the reaction was poured into saturated NaHCO$_3$. The aqueous was extracted with Et$_2$O (3×). The organic extracts were washed with H$_2$O (2×), brine, dried, filtered, and concentrated to dryness. The residue was chromatographed on a Still column and the product eluted with 40% EtOAc-hexanes to yield 5.2 g of 6.

EXAMPLE 4

3-(3-trifuoromethylphenyl)-4-(2-methylthiopyrimidin-4-yl)-6-(N-carbobenzoxypiperidin-4-yl)pyridazine (7)

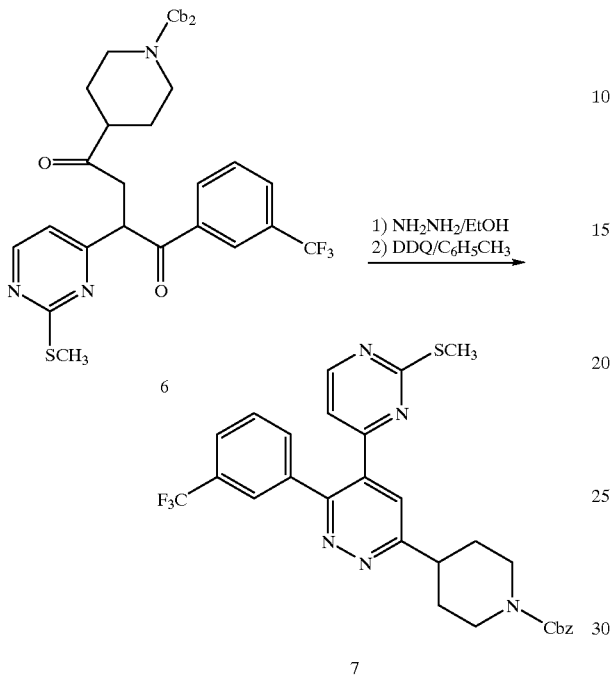

Under Ar, a solution of 6 (5.3 g, 9.3 mmol) in EtOH (150 mL) was stirred at ambient temperatures and then hydrazine (0.6 mL, 19 mmol) was added. After 3 h, the EtOH was concentrated off under reduced pressure (20 mm). The residue was treated with $H_2O$ and the aqueous solution extracted with EtOAc(3x). The combined extracts were washed with brine, dried, filtered and concentrated to dryness. The residue (6.0 g) was dissolved in toluene (180 mL) and treated with DDQ (2.3 g, 10.1 mmol) and dark colored suspension stirred at ambient temperature. After 72 h, the reaction mixture was concentrated to dryness with silica gel (50 g) and the residue placed on a Still column (70 mm) and the product eluted with 70% EtOAc-hexanes to yield 4.6 g of 7.

EXAMPLE 5

3-( 3-trifluoromethylphenyl)-4-( 2-methylsulfonylprimidin-4-yl)-6-(N-carbobenzoxypiperidin-4-yl)pyridazine (8)

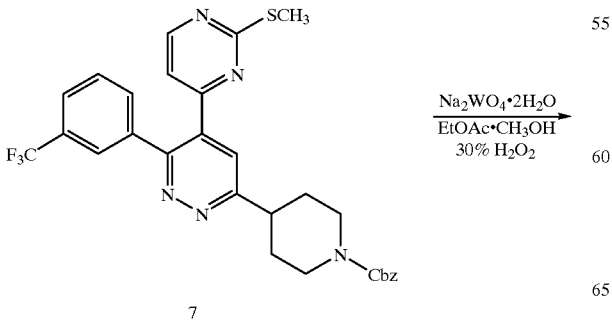

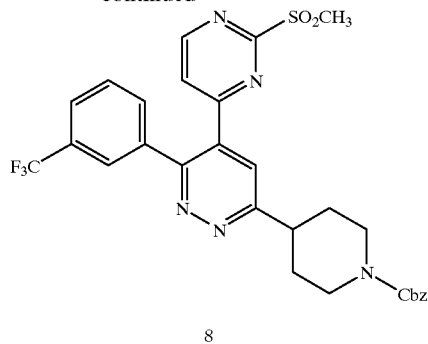

Under Ar, a mixture of 7 (4.6 g, 8.1 mmol), $CH_3OH$ (30 mL), EtOAc (90 mL) and $Na_2WO_4 \cdot 2H_2O$ (360 mg, 1.1 mmol) was stirred at ambient temperature while 30% $H_2O_2$ (3.7 mL., 32.6 mmol) was added. After the addition, the mixture was heated at reflux for 15 h, poured in saturated $NaHCO_3$ solution and the aqueous extracted with EtOAc (3x). The combined organic extracts were backwashed with brine, dried, filtered and concentrated to dryness to yield 4.5 g of 8.

EXAMPLE 6

(S) 3-(trifluoromethylphenyl)-4-[(2-α-methylbenzylamino) pyrimidin-4-yl)]-6-(N-carbobenzoxypiperidin-4 yl)pyridazine (9)

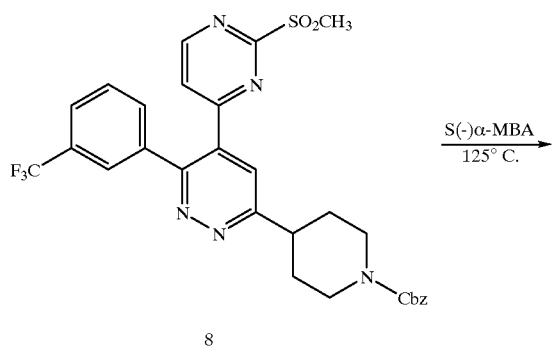

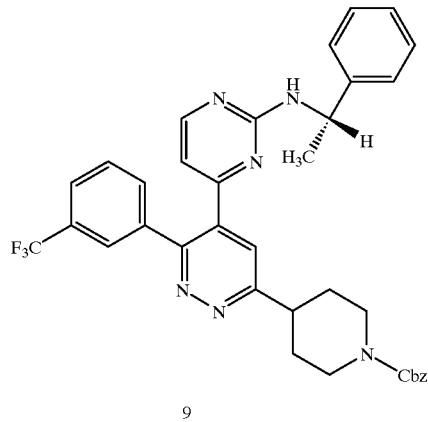

Under Ar, a mixture of 8 (4.5 g, 7.6 mmol) and S (–) α-methylbenzylamine (11.4 mL, 88 mmol) was heated at 125° C. for 3 h. After standing overnight at ambient temperature the mixture was chromatographed on a Still column

EXAMPLE 7

(S) 3-trifluoromethylphenyl-4-[(2-(α-methylbenzylamino) pyrimidin-4-yl]-6-(piperidin-4-yl)pyridazine (10)

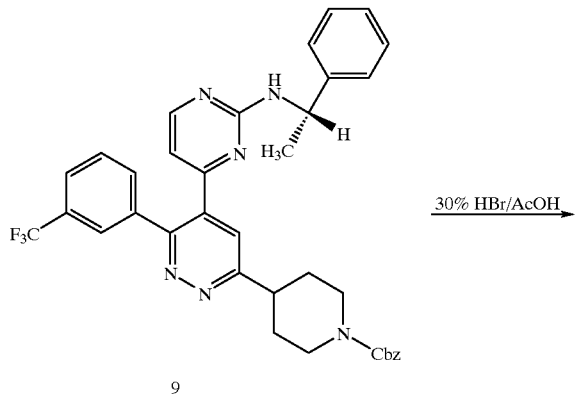

9

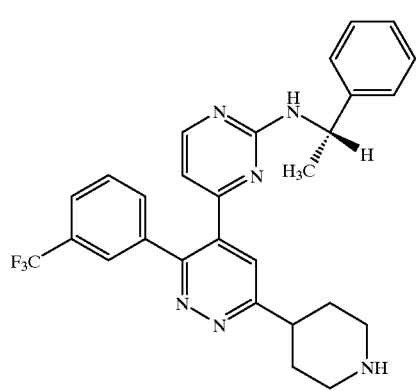

10

Under Ar, a solution of 9 (3.1 g, 4.9 mmol), 30% HBr—AcOH (30 mL) and methylene chloride (10 mL) was stirred at ambient temperature. After 3 h, 3N HCl was added and the solution extracted with Et$_2$O (2×). The aqueous layer was basified with solid Na$_2$CO$_3$ and extracted with EtOAc (3×). The combined extracts were dried, filtered and concentrated to dryness. The residue was dissolved in EtOAc and treated with 1N HCl in Et$_2$O (10 mL) and the solution was concentrated to dryness, triturated with Et$_2$O and filtered to yield 0.46 g of 10.

Analysis calculated for C$_{28}$H$_{27}$N$_6$F$_3$.2HCl.H$_2$O. C, 56.47; H, 5.25; N, 14.11; Found: C, 56.72; H, 5.54; N, 13.61; MS (M+1)=505.5.

EXAMPLE 8

(S) 3-trifluoromethylphenyl-4-[2-(α-methlbenzylamino) pyrimidin-4-yl]-6-(N-methyl) piperidin-4-yl)pyridazine (11)

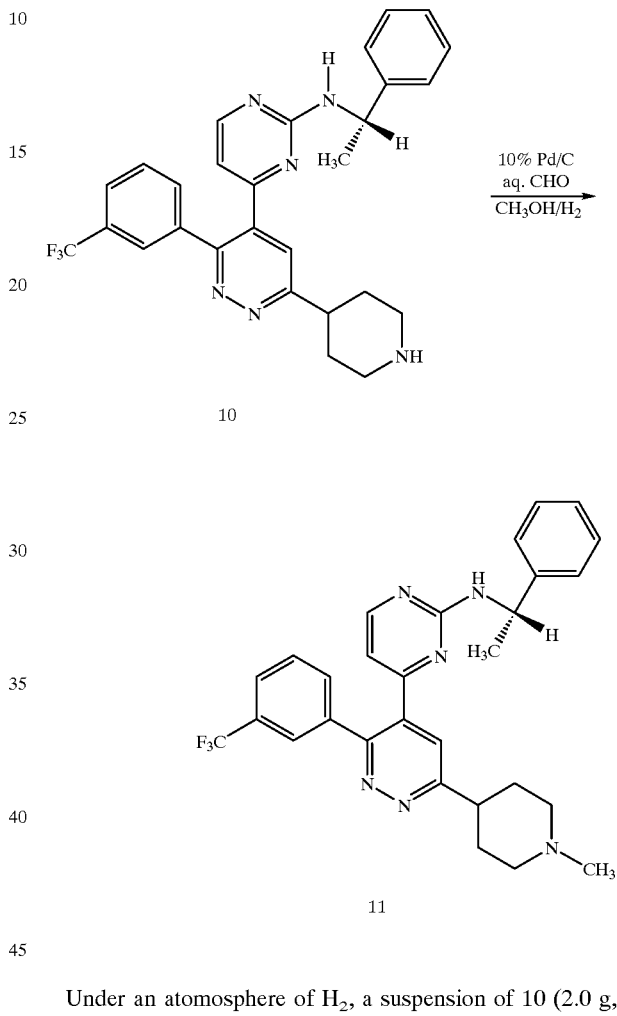

Under an atomosphere of H$_2$, a suspension of 10 (2.0 g, 4 mmol), methanol (30 mL), 36–38% aqueous formaldehyde (2.2 mL) and 10% Pd on carbon (370 mg) was stirred at ambient temperature. After 20 h, the suspension was filtered under an atmosphere of N$_3$ through celite, and the filtrate was concentrated to dryness. The residue was chromatographed an a Still column (80 mm) and the product eluted with 2.5% methanol-chloroform saturated with NH$_3$. The common fractions were concentrated to dryness and the residue treated with 3N HCl. The aqueous solution was extracted with Et$_2$O (2×), basified, and extracted with EtOAc (3×). The EtOAc layers were dried, filtered and concentrated to dryness. The residue was dissolved in methylene chloride-cyclohexane and treated with 1N HCl in Et$_2$O. The solution was concentrated to dryness and the residue triturated with Et$_2$O, filtered and dried in vacuo to yield 0.9 g of 11.

Analysis calculated for C$_{29}$H$_{29}$F$_3$N$_6$.HCl. 1.5H$_2$O. C, 59.84; H, 5.71; N, 14.44. Found: C, 59.88; H, 5.33; N,14.19. MS (M+1) 519.3.

EXAMPLE 9

4-(3-trifluoromethylphenyl)-4-oxo-3-(pyridin-4yl)-1-oxo-1-(N-carbobenzoxypiperidin-4-yl)butane (13)

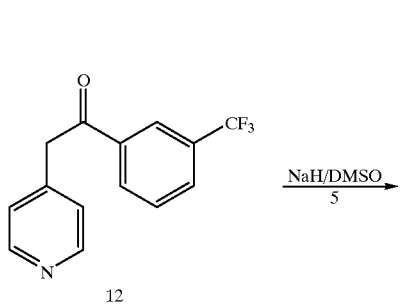

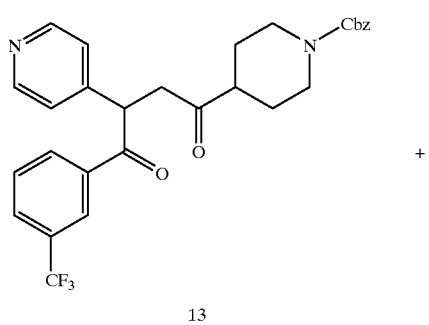

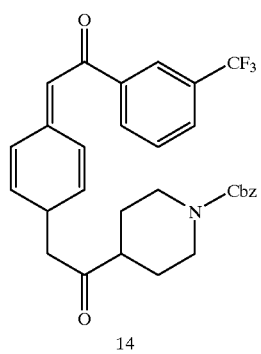

Under Ar, a solution of 12 (8.1 g, 30.6 mmol) in DMSO (100 mL) was treated with 95% NaH (0.9 g, 35.5 mmol) and stirred at ambient temperature. After 1 h, a solution of 5 (9.1 g, 30.7 mmol) in DMSO (100 mL) was added dropwise. After 18 h, 2N AcOH (100 mL) was added and the solution then poured carefully into a saturated $Na_2CO_3$ solution. The aqueous solution was extracted with EtOAc (4×). The combined organics were backwashed with saturated $Na_2CO_3$, water, brine, and dried, filtered and concentrated to dryness. The residue was triturated with $Et_2O$, and then filtered to yield 8.6 g (54%) of 14 as a yellow-orange solid. The mother liquor was chromatographed on a Still column (100 mm) and the product eluted with 65–90% EtOAc-hexanes to yield 2.2 g of 13.

EXAMPLE 10

3-(3-trifluoromethylphenyl)-4-(pyridin-4-yl)-6-(N-carbobenzoxypiperidin-4-yl)pyridazine (15)

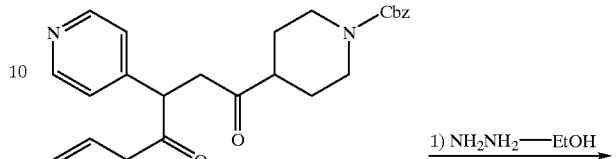

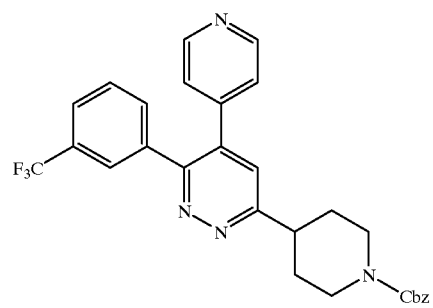

Under Ar, a solution of 13 (2.2 g, 4.2 mmol) in EtOH (50 mL) was treated with hydrazine (306 mg, 9.6 mmol). After 4 h, the reaction was concentrated to dryness and the residue was partitioned between water-EtOAc (3×). The EtOAc extracts were backwashed with brine, dried, filtered and concentrated to dryness. The residue was dissolved in toluene (60 mL) and 2,3 dichloro-5,6-dicyano-1,4-benzoquinone (DDQ) (1.0 g, 4.5 mmol) was added. After 0.5 h, the reaction was chromatographed on a Still column (60 mm) and the product eluted with 90–100% EtOAc-hexanes to yield 1.6 g of 15.

EXAMPLE 11

3-(3-trifluoromethylphenyl)-4(pyridine-4-yl)-6-(N-methylpiperidin-4-yl)pyridazine (16)

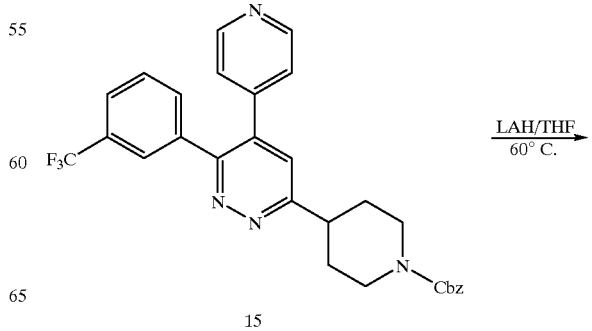

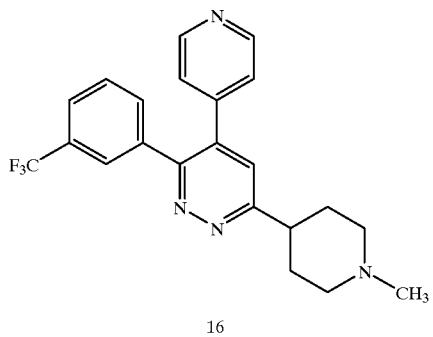

16

Under Ar, a solution of 15 (0.73 g, 1.4 mmol) in THF (175 mL) was treated with LAH (0.37 g, 9.7 mmol). After addition, the reaction was heated at 60° C. After 2 h, the reaction was cooled to room temperature and treated with saturated Na$_2$SO$_4$ until a suspension results. The reaction mixture was filtered and the filtrate washed with EtOAc. The organic was washed with H$_2$O, brine, dried, filtered and concentrated to dryness. The residue was treated with Et$_2$O-hexanes, filtered and dried to yield 0.3 g of 16; mp 188–9° C.

Analysis calculated for C$_{22}$H$_{21}$N$_4$F$_3$; C,64.99; H,5.43; N,13.78. Found: C, 65.29; H,5.83; N,14.06.

EXAMPLE 12

3-(trifluromethylphenyl)-4-(pyridin-4-yl)-6-(piperidin-4-yl) pyridazine (17)

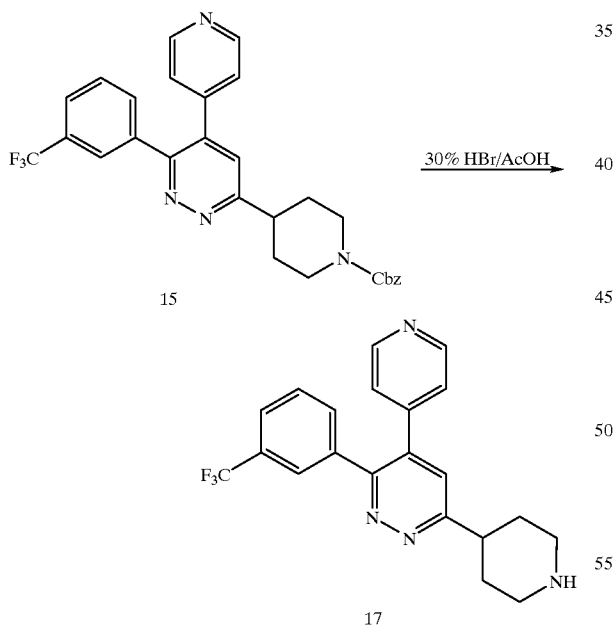

Under Ar, a mixture of 15 (0.87 g, 17 mmol) in 30% HBr in AcOH (10 mL) was stirred at ambient temperatures. After 1.5 h, the reaction was poured into 3N HCl and extracted with Et$_2$O (2×). The aqueous layer was basified carefully with a saturated Na$_2$CO$_3$ solution until basic and then extracted with EtOAc (3×). The combined EtOAc layers were dried, filtered and concentrated to dryness. The residue was chromatographed on a Still column (50 mm) and the product eluted with chloroform saturated with NH$_3$ to yield 0.4 g of 17. The product was treated with 1N HCl in EtOH, concentrated to dryness and triturated with Et$_2$O, filtered and dried to yield the hydrochloride salt; mp 218–20° C.

Analysis calculated for C$_{21}$H$_{19}$F$_3$N$_4$.3 HCl.½ H$_2$O. C, 50.16; H, 4.61; N, 11.14. Found: C, 49.96; H, 4.76; N, 11.15.

EXAMPLE 13

4-(3-trifluoromethylphenyl)-4-oxo-3-(2-fluoropyridin-4-yl)-1-oxo-1-(N-carbobenzoxypiperidin-4-yl)butane (19)

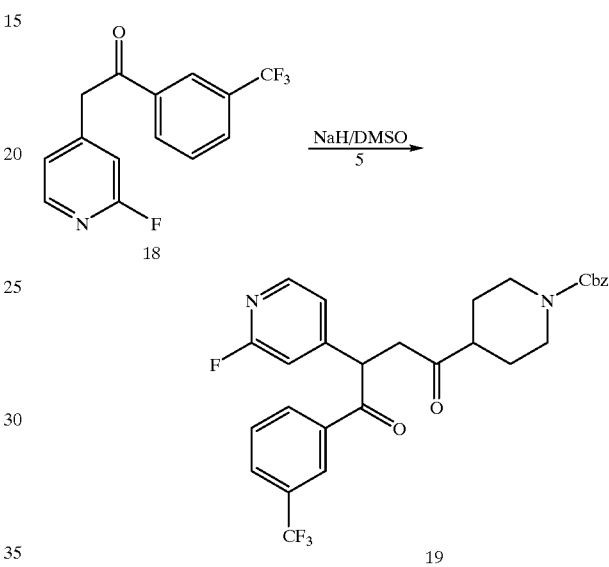

Under Ar, a solution of 18 (4.0 g, 14,1 mmol) in DMSO (30 mL) was treated with 95% NaH (0.4 g, 15.8 mmol) while the reaction was stirred at room temperature. After a ½ h, a solution of 5 (5.0 g, 16.9 mmol.) in DMSO (40 mL) was added dropwise and the solution stirred at room temperature. After 18 h, the reaction was poured into 2N HCl (50 mL) and then basified with saturated Na$_2$CO$_3$ and then extracted with EtOAc (3×). The organic extracts were backwashed with H$_2$O, brine, dried, filtered and concentrated to dryness to yield 8.8 g of 19.

EXAMPLE 14

3-(3-trifluoromethylphenyl) 4-(2-fluoropyridin-4-yl)-6-(N-carbobenzoxypiperidin-4-yl)pyridazine (20)

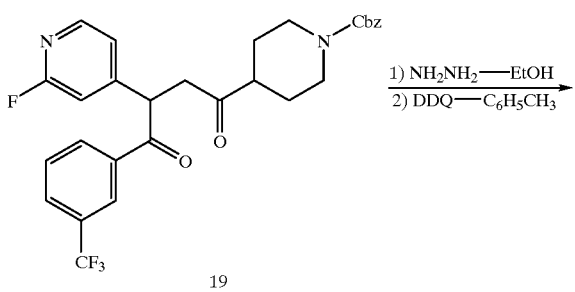

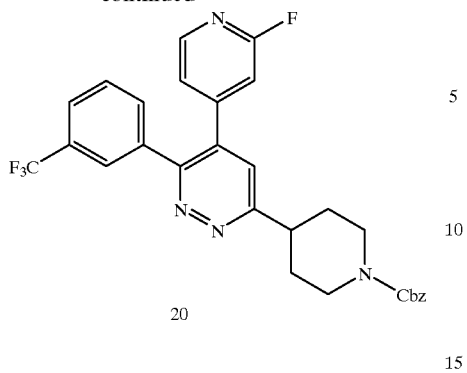

20

Under Ar, a solution of 19 (8.8 g, 14.1 mmol) in EtOH (270 mL) was stirred at room temperature and treated with hydrazine (1.4 g, 42.1 mmol). After 2 h, the reaction was concentrated to dryness. The reaction was partitioned between H₂O and EtOAc (3×). The organic extracts were backwashed with brine, dried, filtered and concentrated to dryness. The residue was dissolved in toluene (400 mL) and treated with DDQ (3.4 g, 14.9 mmol). After stirring at room temperature for 3 h, the reaction was concentrated to dryness. The residue was chromatographed on a Still column (100 mm) and the product eluted with 60% EtOAc-hexanes to yield 5.5 g of 20.

EXAMPLE 15

(S) 3-(3-trifluoromethylphenyl) 4-[(2-(α-methylbenzlamino) pyridin-4-yl]-6-(N-carbobenzoxpiperidin-4-yl pyridazine (21)

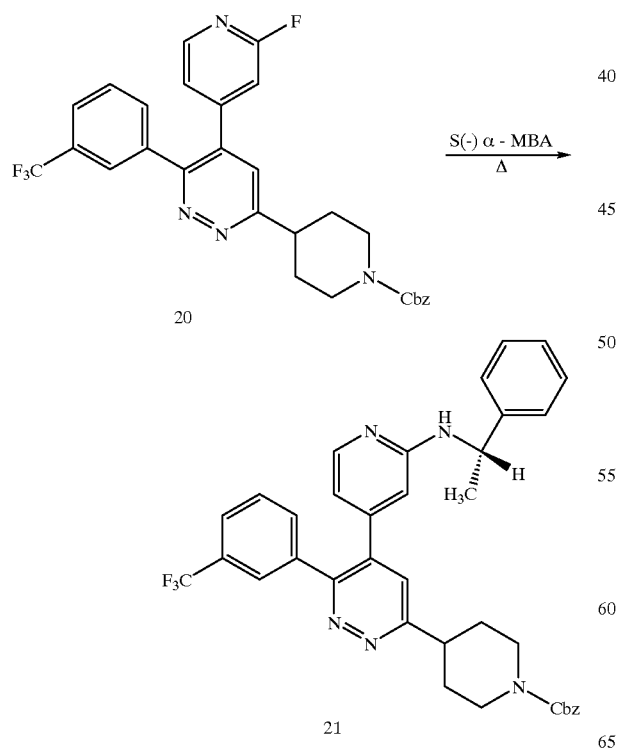

Under Ar, a mixture of 20 (1.6 g, 3.0 mmol) and S (−) α-methylbenzylamine (8 mL) was heated at 180° C. for 1.0 h. The reaction was then chromatographed on a Still column (100 mm) and the product elected with 50–60% EtOAc-hexanes to yield 1.0 g of 21.

EXAMPLE 16

(S) -3-(3-trifluoromethylphenyl)-4-[(3-(α-methyl benzylamino)pyridin-4-yl]-6-(piperidin-4-yl) pyridazine (22)

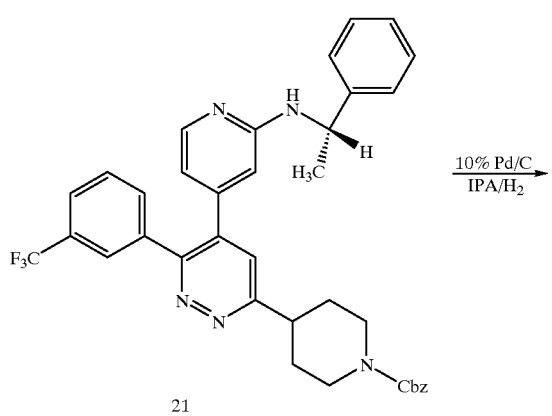

A solution of 21 (0.7 g, 1.1 mmol) in isopropanol (50 mL) was placed in a Parr apparatus under Ar, and 10% Pd on C (200 mg) was added. The suspension was hydrogenated at 6 psi of H₂. After shaking overnight on the Parr apparatus, the suspension was filtered under Ar through super-cel and the pad washed with EtOAc. The filtrate was concentrated to dryness. The residue was chromatographed on a Still column (50 mm) and the product eluted with 3% CH₃OH-chloroform saturated with NH₃ to yield 0.24 g of 22.

Analysis calculated for $C_{29}H_{28}F_3N_5 \cdot 0.25 H_2O$. C, 68.55; H, 5.65; N, 13.79. Found: C, 68.36; H, 5.67; N, 13.75. MS (M+1)=504.2612

EXAMPLE 17

(S) 3-(3-trifluoromethylphenyl)-4-[2-(α-methylbenzlamino) pyridin-4-yl]-6-(N-methylpiperidin-4-yl)pyridazine (23)

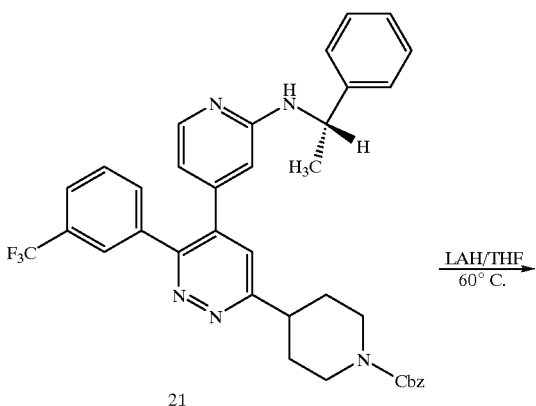

Under Ar, a solution of 21 (0.8 g, 1.2 mmol) in THF (50 mL) was treated with LAH (0.3 g, 7.9 mmol) and heated to 50° C. After 2 hrs, the reaction was cooled to room temperature and treated with saturated $Na_2SO_4$ until a white suspension resulted. The suspension was filtered through super-cel and the pad washed with EtOAc. The organic extracts were concentrated to dryness and the residue chromatographed on a Still column (50 mm) and the product eluted with chloroform saturated with $NH_3$. The residue was dissolved in EtOAc and treated with 1N HCl in $Et_2O$ concentrated to dryness and the residue was stirred with 1:1 EtOAc-$Et_2O$ (20 mL), cooled in an ice bath and filtered. The solid was dried in vacuo to yield 350 mg of 23.

Analysis calculated for $C_{30}H_{30}F_3N_5 \cdot 2HCl \cdot 1.5\ H_2O$. C, 58.34; H, 5.71; N, 11.34. Found: C, 58.56; H, 5.82; N, 10.72. MS(M+1)=518.31.

EXAMPLE 18

1-(2-methylthiopyrimidin-4-yl)-1-oxo-2-(3-trifluoromethylphenyl)ethane (25)

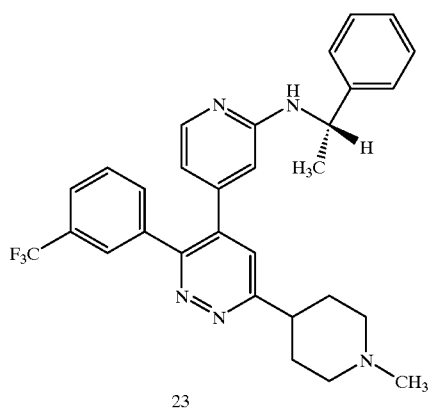

Under Ar, a solution of 3-trifluoromethylbenzyl chloride (12 mL, 77 mmol) in $Et_2O$ (75 mL) was added dropwise to a mixture of Mg turnings (1.7 g, 71 mmol), $Et_2O$ (75 mL) and cat. $I_2$. The mixture was heated at reflux for 0.5 h, stirred at room temperature over 1 h and then a solution of 24 (9.3 g, 44 mmol) in $Et_2O$ (75 mL) was added dropwise. After refluxing for 4 h, the reaction was cooled to room temperature and treated with 2N HCl. The aqueous was extracted with $Et_2O$ (1×) and EtOAc (2×). The combined extracts were backwashed with $H_2O$, brine, dried, filtered and concentrated to dryness. The residue was chromatographed on a Still column (100 mm) and the product eluted with 20% EtOAc-hexanes to yield 3.5 g of 25.

EXAMPLE 19

1-(2-methylthiopyrimidin-4-yl)-1-oxo-2-(3-trifluoromethylphenyl)-4-oxo-4-(N-carbobenzoxypiperidin-4-yl)butane (26)

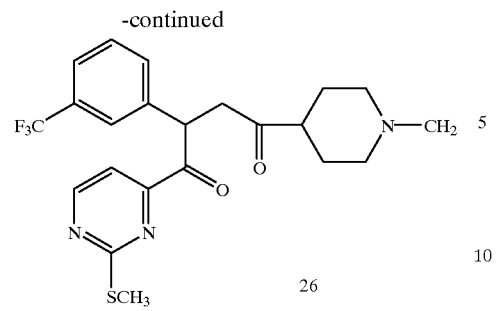

Under Ar, a solution of 25 (4.0 g, 12.8 mmol) in DMSO (30 mL) was treated with 95% NaH (0.35 g, 13.8 mmol). After stirring at room temperature for 15 min, a solution of 5 (3.9 g, 13.2 mmol) in DMSO (20 mL) was added in one portion to the deep red solution. After stirring at room temperature for 18 h, 2N AcOH was added and then poured carefully in saturated Na$_2$CO$_3$. The basic aqueous solution was extracted with EtOAc (3×). The organic extracts were backwashed with H$_2$O, brine, dried, filtered and concentrated to dryness. The residue was chromatographed on a Still column (80 mm) and the product was eluted with 30% EtOAc-hexanes to yield 1.5 g of 26.

EXAMPLE 20

3-(2-methylthiopyrimidin-4-yl)-4-(3-trifluoromethylphenyl)-6-(N-carbobenzoxypiperidin-4-yl)peridazine (27)

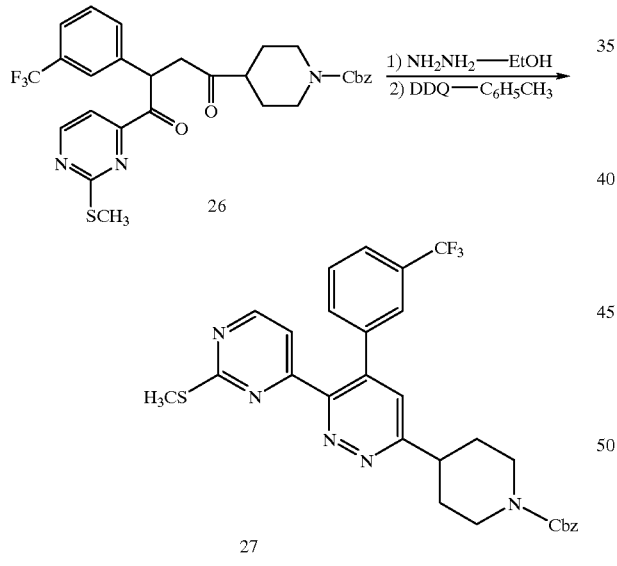

Under Ar, a solution of 26 (1.5 g, 2.6 mmol) in EtOH (50 mL) was treated with hydrazine (0.5 mL, 16 mmol). After 5 h, the reaction was concentrated to dryness. The residue was treated with H$_2$O and extracted with EtOAc (3×). The EtOAc extracts were dried, filtered and concentrated to dryness. The residue was dissolved in toluene (100 mL) and treated with DDQ (0.62 g, 2.7 mmol). After 0.5 h, the dark colored reaction was concentrated to dryness. The residue was chromatographed on a Still column (50 mm) and the product eluted with 40% EtOAc-hexanes to yield 1.2 g of 27.

EXAMPLE 21

3-(2-methylsulfonylpyrimidin-4-yl)-4-(3-trifluoromethylphenyl)-6-(N-carbobenzoxypiperidin-4-yl)pyridazine (28)

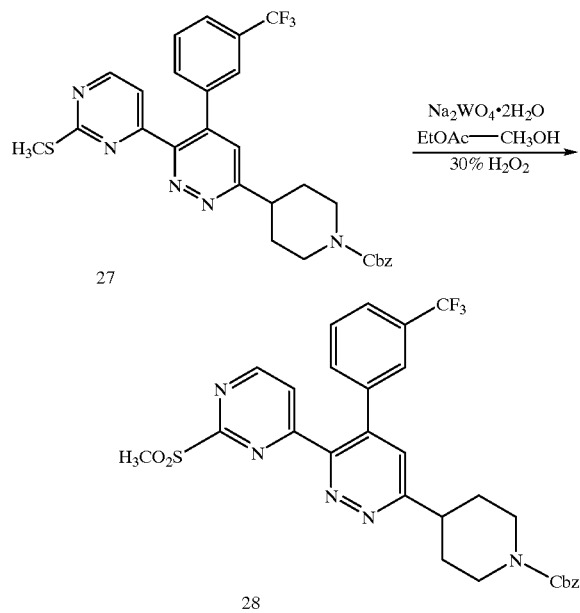

Under Ar, a solution of 27 (1.2 g, 2.1 mmol) in CH$_3$OH (10 mL) and EtOAc (30 ml) was added Na$_2$WO$_4$.2H$_2$O (100 mg, 0.3 mmol) and 30% H$_2$O$_2$ (1.3 mL, 11 mmol) and the mixture heated at reflux. After 18 h, a saturated solution of NaHSO$_3$ was added to destroy excess peroxides and the aqueous extracted with EtOAc (3×). The organic extracts were dried, filtered and concentrated to dryness. The residue was chromatographed on a Still column (60 mm) and the product eluted with 90% EtOAc-hexanes to yield 0.61 g of 28.

EXAMPLE 22

(S) 3-[2-(α-methylbenzylamino)pyrimidin-4-yl]-4-(3-trifluoromethylphenyl)-6-(N-carbobenzoxypiperidin-4-yl)pyridazine (29)

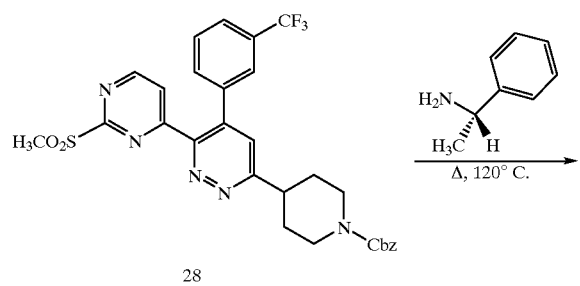

-continued

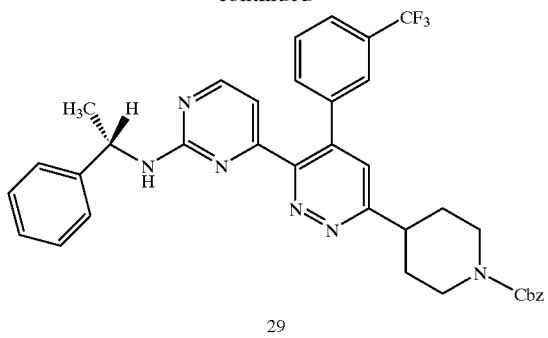

29

Under Ar, a mixture of 28 (0.62 g, 1.0 mmol) and (S) (−)-α-methylbenzylamine (1.5 mL, 11.6 mmol) was heated at 120 ° C. for 3 h. The reaction was chromatographed on a Still column (40 mm) and the product eluted with 80% EtOAc-hexanes to yield 0.6 g of 29.

EXAMPLE 23

(S) 3-[2-(α-methylbenzylamino )pyrimidin-4-yl]-4-(3-trifluoromethylphenyl)-6-(piperidin-4-yl)pyridazine (30)

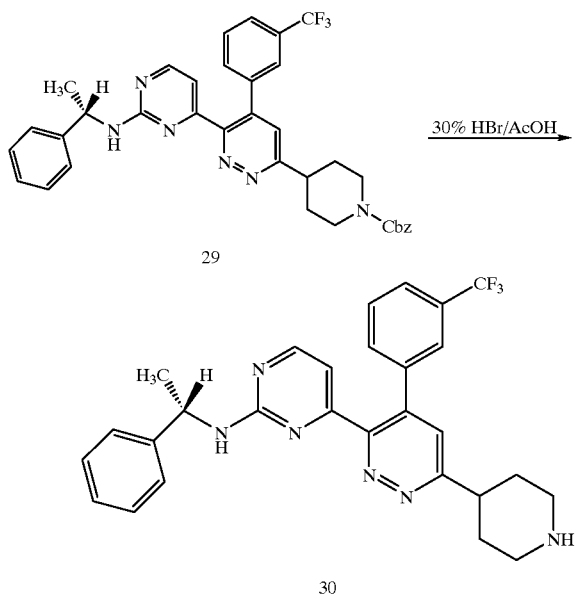

Under Ar, a solution of 29 (0.3 g, 0.47 mmol) in 30% HBr-AcOH (5 mL) was stirred at room temperature for 1 h. The reaction was then treated with 2N HCl and extracted with Et$_2$O (2×). The resulting aqueous was then basified with saturated Na$_2$CO$_3$ and extracted with EtOAc (3×). The organic extracts were dried, filtered and concentrated to dryness. The residue was chromatographed on a Still column (40 mm) and the product eluted with 5% CH$_3$OH CHCl$_3$ saturated with NH$_3$ to yield 70 mg of 30.

Analysis calculated for C$_{28}$H$_{27}$F$_3$N$_6$·H$_2$O. C, 63.26; H, 5.88; N, 15.81; Found: C, 63.82; H, 5.40; N, 15.33; Mass spectra (M+1)=505.21.

EXAMPLE 24

(S) 3-[2-(α-methylbenzylamino)pyrimidin-4-yl]-4-(3-trifluoroethylphenyl)-6-(N-ethylpiperidin-4-yl)pyridazine (31)

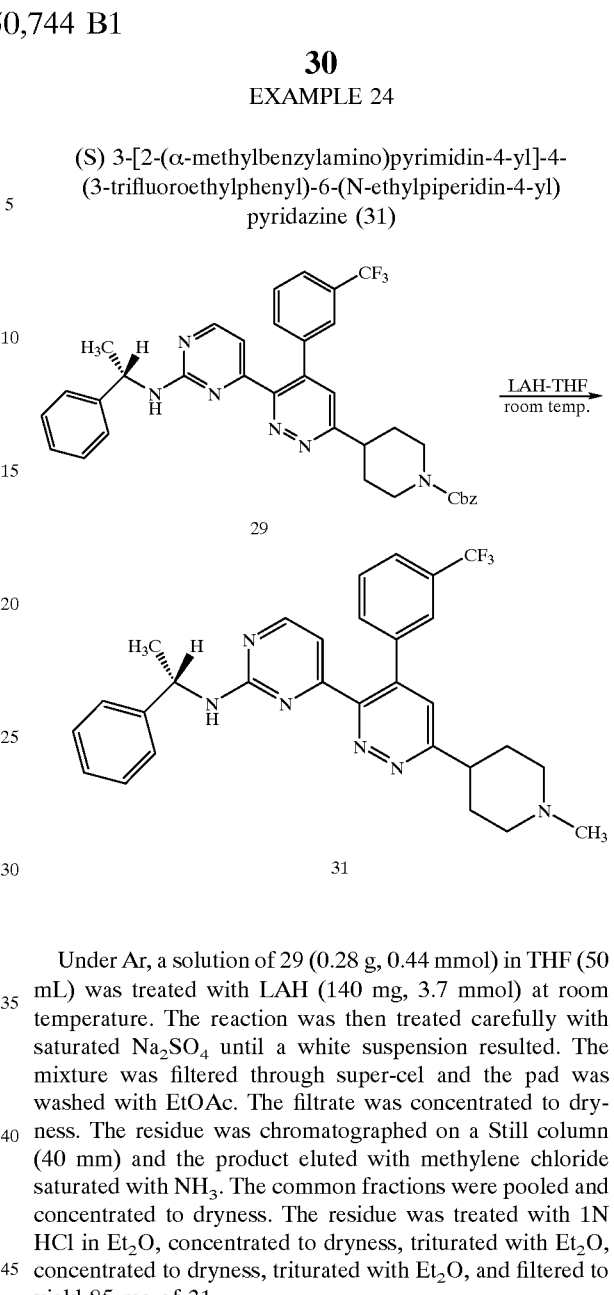

Under Ar, a solution of 29 (0.28 g, 0.44 mmol) in THF (50 mL) was treated with LAH (140 mg, 3.7 mmol) at room temperature. The reaction was then treated carefully with saturated Na$_2$SO$_4$ until a white suspension resulted. The mixture was filtered through super-cel and the pad was washed with EtOAc. The filtrate was concentrated to dryness. The residue was chromatographed on a Still column (40 mm) and the product eluted with methylene chloride saturated with NH$_3$. The common fractions were pooled and concentrated to dryness. The residue was treated with 1N HCl in Et$_2$O, concentrated to dryness, triturated with Et$_2$O, concentrated to dryness, triturated with Et$_2$O, and filtered to yield 85 mg of 31.

Analysis calculated for C$_{29}$H$_{29}$F$_3$N$_6$·2HCl·1.25 H$_2$O. C, 56.72; H, 5.50; N, 13.69. Found: C, 56.94; H, 5.67; N, 13.04. MS (M+1)=519.27.

EXAMPLE 25

1-(pyridin-4-yl)-1-oxo-2-(3-trifluoromethylphenyl)ethane (33)

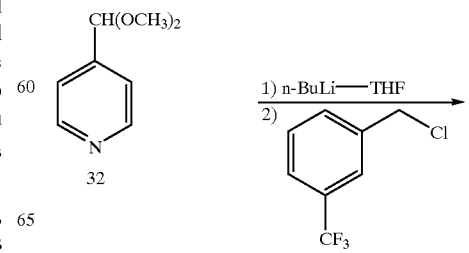

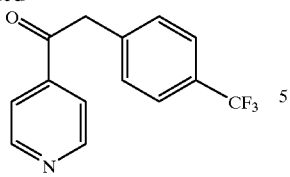

33

Under Ar, a solution of 32 (5.0 g, 32.7 mmol) in THF (50 mL) was cooled to −78° C. and treated dropwise with 2.5N n-BuLi in hexane (14 mL, 35 mmol). After the addition, the solution was stirred for 15 min at −78° C. and then 3-trifluormethylbenzyl chloride (5.4 mL, 6.8 g, 35 mmol) was added dropwise. After the addition, the solution was stirred at 0–4° C. and the deep purple color diminished to a light amber color. After 2 h, the reaction was stirred at room temperature for 1 h and then poured into saturated NaHCO$_3$, and extracted with EtOAc (3×). The organic extracts were backwashed with brine, dried, filtered and concentrated to dryness. The residue was treated with formic acid (116 mL) and the mixture heated at 80° C. After 2 h, the reaction was concentrated to dryness. The residue was partitioned between EtOAc (3×)—saturated NaHCO$_3$. the organic extracts were backwashed with brine, dried, filtered and concentrated to dryness. The residue was chromatographed on a Still column (70 mm) and the product eluted with 50% EtOAc-hexanes to yield 5.0 g (57%) of 33.

EXAMPLE 26

1-(pyridin-4-yl)-1-oxo-2-(3-trifluoromethylphenyl)-4-oxo-4-(N-carbobenzoxypiperidin-4-yl)butane (34)

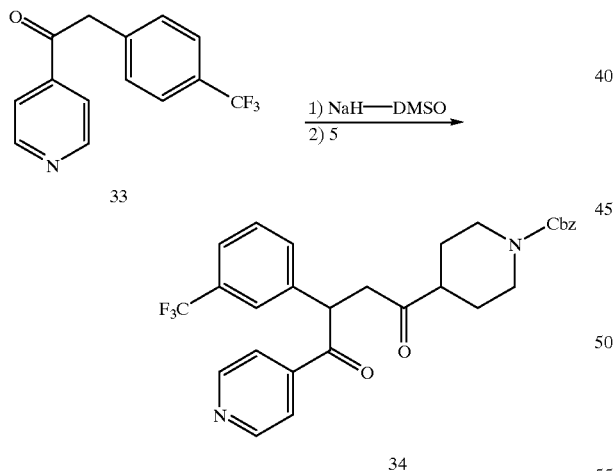

Under Ar, a solution of 33 (5.2 g, 19.6 mmol) in DMSO (65 mL) was stirred at room temperature and treated with 95% NaH (0.58 g, 22.8 mmol). After 1 h, a solution of 5 (5.8 g, 19.6 mmol) in DMSO (25 mL) was added dropwise. After 18 h, the reaction was poured into 2N HCl (100 mL) and then basified with saturated Na$_2$CO$_3$ and then extracted with EtOAc (3×). The combined EtOAc extracts were backwashed with H$_2$O, brine, dried, filtered and concentrated to dryness. The residue was chromatographed on a Still column to yield 3.3 g of crude 34.

EXAMPLE 27

3-(pyridin-4-yl)-4-(3-trifluoromethylphenyl)-6-(N-carbobenzoxypiperidin-4-yl)pyridazine (35)

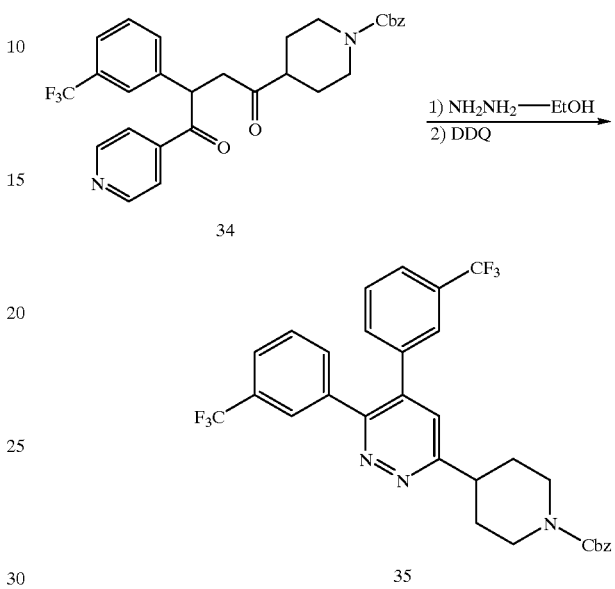

Under Ar, hydrazine (0.5 mL, 0.51 g, 15.9 mmol) was added to a solution of 34 (3.3 g) in EtOH (75 mL). After 4 h, the solution was concentrated to dryness and the residue treated with toluene (60 mL) dioxane (60 mL) and DDQ (0.8 g, 3.5 mmol). After 15 h, the reaction was concentrated to dryness. The residue was chromatographed on a Still column (50 mm) and the product eluted with 100% EtOAc to yield 1.2 g of 35.

EXAMPLE 28

3-(pyridine-4-yl)-4-(3-trifluoromethylphenyl)-6-(piperidin-4-yl)pyridazine (36)

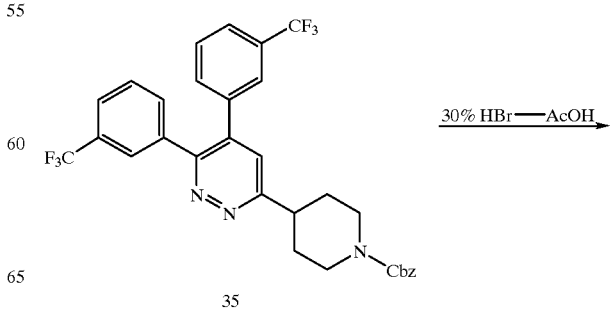

EXAMPLE 30

2-(2-methylsulfonylpyrimidin-4-yl)-3-(3-trifluoromethylphenyl)pyrazine (39)

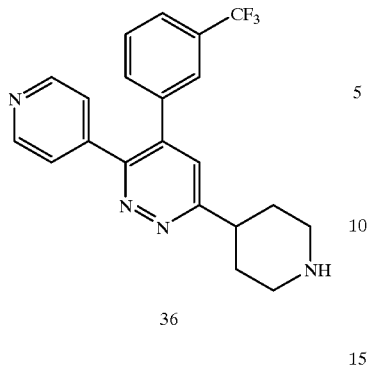
36

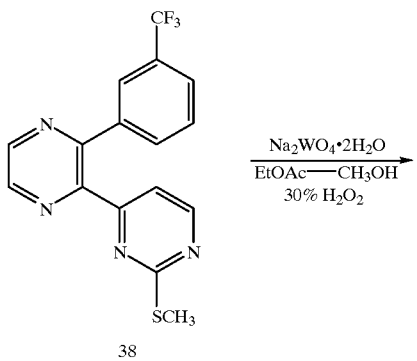

Under Ar, a mixture of 35 (0.68 g, 1.3 mmol) and 30% HBr—AcOH (10 mL) was stirred at room temperature. After 3 h, 3N HCl (50 mL) was added and the solution extracted with Et$_2$O (2×). The aqueous layer was basified with saturated Na$_2$CO$_3$ and extracted with EtOAc (6×). The organic extracts were dried, filtered and concentrated to dryness. The residue was crystallzed from EtOAc-hexanes to yield 73 mg (15%) of 36 mp 148–50° C.

Analysis calculated for C$_{21}$H$_{19}$F$_3$N$_4$.2.5 H$_2$O. C, 58.73; H, 5.63; N, 13.05. Found: C, 58.85; H, 5.10; N, 12.04.

EXAMPLE 29

2-(2-methylthiopyrimidin-4-yl)-3-(3-trifluoromethylphenyl)pyrazine (2)

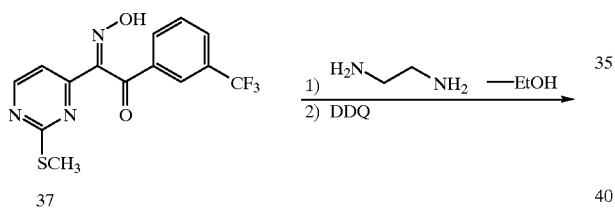
37

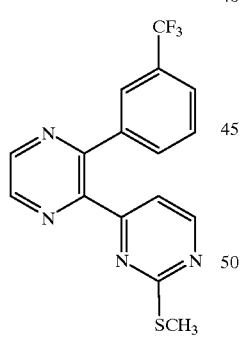
38

Under Ar, a solution of oxime 37 (1.0 g, 2.9 mmol) in abs. EtOH (30 mL) with ethylene diamine (0.27 g, 4.5 mmol) and AcOH (4 drops) was heated at reflux. After 3 days, the reaction mixture was concentrated to dryness and partitioned between saturated NaHCO$_3$ and EtOAc (3×). The organic extracts were dried, filtered and concentrated to dryness. The residue was dissolved in toluene (80 mL) and treated with DDQ (0.66 g, 2.9 mmol). After stirring at room temperature overnight, the suspension was chromatographed on a Still column (50 mm) and the product eluted with 30% EtOAc-hexanes to yield 100 mg (10%) of 38.

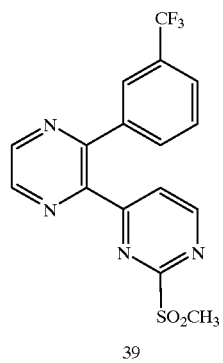
39

Under Ar, a solution of 38 (290 mg, 0.83 mmol) in CH$_3$OH (2 mL) and EtOAc (9 mL) was treated with sodium tungstate dihydrate (55 mg, 0.17 mmol) and 30% H$_2$O$_2$ (0.5 mL, 4.4 mmol). After stirring at reflux for 15 h, the reaction was treated with saturated NaHSO$_3$ and extracted with EtOAc (3×). The organic extracts were dried, filtered and concentrated to dryness to yield 0.28 (89%) g of 39.

EXAMPLE 31

S-[2-(α-methylbenzylamino)pyrimidin-4yl]3-(3-trifluoromethlphenyl)pyrazine (40)

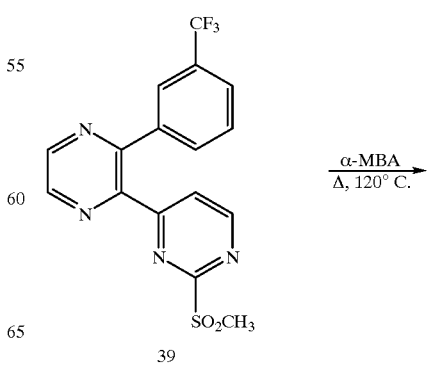
39

35
-continued

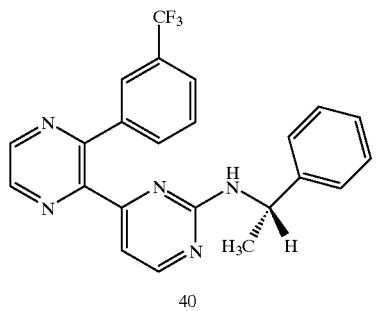

40

Under Ar, sulfone 39 (0.28 g, 0.74 mmol) and 5-(-)
α-methylbenzylamine (0.97 g, 8 mmol) were heated at 120°
C. After 20 h, the mixture was chromatographed on a Still
column (50 mm) and the product eluted with 30–40%
EtOAc-hexanes. The residue was treated with EtOAc and
1N HCl (3 mL), concentrated to dryness, triturated with
hexanes and filtered to yield 160 mg of 40.

Analysis calculated for $C_{23}H_{18}F_3N_5$-.HCl.0.4 Hex.0.5
$H_2O$. C, 60.9; H, 4.85; N, 13.61; Found: C, 60.84; H, 5.15;
N, 13.97; MS (M+1)=422.1.

EXAMPLE 32

1-(2-fluoropyridin-4-yl)1,2-dioxo-2-(3-trifluoromethylphenyl)ethane (42)

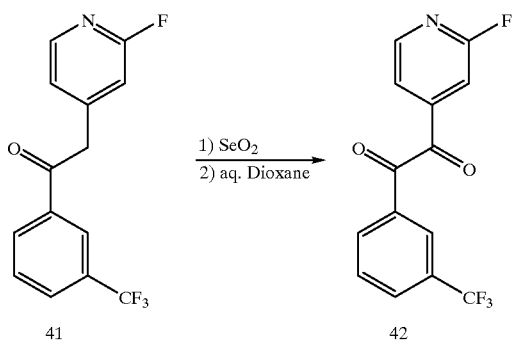

Under Ar, a solution of 41 (6.4 g, 22.6 mmol) in 5%
aqueous dioxane (100 mL) was treated with $SeO_2$ (9.5 g,
86.5 mmol) and the mixture heated at reflux with stirring.
After 2 h, the reaction was cooled to room temperature and
concentrated to dryness. The residue was dry packed with
silica gel (50 g) and chromatographed on a Still column (70
mm). The product was elected with 15% EtOAc-hexanes to
yield 3.35 g of 42.

36

EXAMPLE 33

2-(2-fluoropyridin-4-yl)-3-(3-trifluoromethylphenyl)
pyrazine (43)

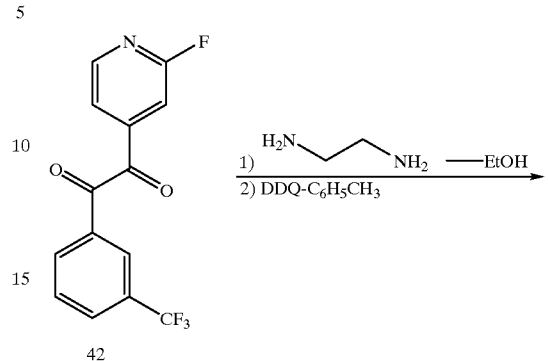

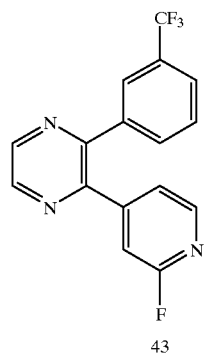

Under Ar, a solution of 42 (3.35 g, 11.3 mmol) in EtOH
(150 mL) was treated with ethylene diamine (0.9 g, 15
mmol) and heated at 50° C. After 3 h, the reaction was
concentrated to dryness and the residue was partitioned
between $H_2O$ and EtOAc (3×). The combined organic
extracts were dried, filtered and concentrated to dryness. The
residue was dissolved in toluene (230 mL) and reacted with
DDQ (4.0 g, 17.6 mmol). After 18 h at room temperature, the
reaction was heated at 60° C. for 2 h then treated with
additional DDQ (1.0 g) and heated at 80° C. for 5 h. The
reaction was then dry packed with silica gel (70 g) and
chromatographed on a Still column (80 mm). The product
was eluted with 30% EtOAc-hexanes to yield 2.85 g of 43.

EXAMPLE 34

(S)-2-[2-(α-methylbenzylaminopyridin-4-yl]-3-(3-trifluoromethylphenyl)pyrazine (44)

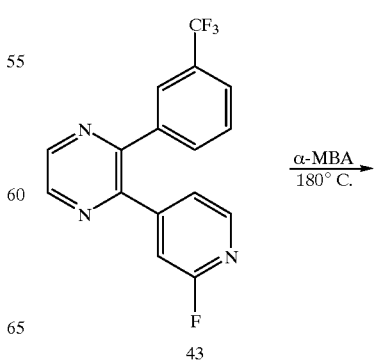

-continued

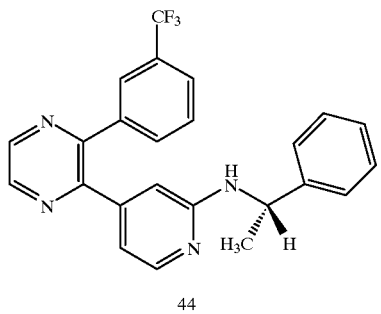

44

Under Ar, a mixture of 43 (1.1 g, 3.4 mmol) and S-(−)-α-methylbenzylamine (4.7 g, 37 mmol) was heated at 180° C. After 6 h, the mixture was chromatographed on a Still column (60 mm) and the product eluted 50% EtOAc-hexanes. The residue was treated with ethanolic-HCl, concentrated to dryness and the residue pumped dry to yield 1.2 g. of 44 as a glass.

Analysis calculated for $C_{24}H_{19}F_3N_4 \cdot HCl \cdot 4s$ ½ $H_2O$. C, 61.87; H, 4.54; N, 12.03. Found: C, 62.12; H, 5.02; N, 11.68. MS (M+1)=421.21.

EXAMPLE 35

1-(pyridin-4-yl)-1,2-dioxo-2-(3-trifluoromethylphenyl) ethane (46)

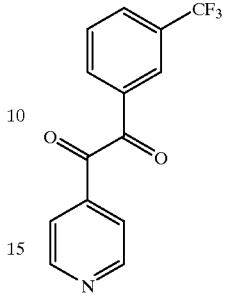

Under Ar, a solution of 45 (7.7 g, 29 mmol) in 5% aqueous dioxane (130 mL) was treated with $SeO_2$ (12.2 g, 110 mmol) and heated at reflux. After 2 h, the reaction was filtered through super-cel and the pad washed with EtOAc. The filtrate was dry packed on silica gel (200 mL) and chromatographed on a Still column (80 mm). The product was eluted with 50% EtOAc-hexanes to yield 2.3 g of 46.

EXAMPLE 36

2-(pyridine-4-yl)-3-(3-trifluoromethylphenyl) pyrazine (47)

Under Ar, a solution of 46 (2.3 g, 8.2 mmol) in abs. EtOH (100 mL) was treated with ethylene diamine (0.58 g, 9.6 mmol) and heated at 50° C. After 18 h, the solution was concentrated to dryness. The residue was partitioned between $H_2O$ and EtOAc (3x) and the organic extracts were dried, filtered and concentrated to dryness. The residue was treated with toluene (125 mL) and DDQ (3.8 g, 16.7 mmol) and then heated to 80° C. After 18 h, the reaction was concentrated to dryness. The residue was dry packed with silica gel (100 mL) and chromatographed on a Still column (80 mm). The product was eluted with EtOAc and the common fraction concentrated to dryness. The residue was treated with $Et_2O$ and ethanolic-HCl and concentrated to dryness. The residue was triturated from EtOAc and filtered to yield 100 mg of 47.

Analysis calculated for $C_{16}H_{10}F_3N_3 \cdot HCl$. C, 56.90; H, 3.28; N, 12.44. Found: C, 56.45; H, 3.63; N, 12.09; MS (M+1)=302.1.

The ability of compounds of the present invention to inhibit the synthesis or the activity of cytokines can be demonstrated using the following in vitro assays.

BIOLOGICAL ASSAYS

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours. at 37° C. in 5% $CO_2$. At the end of the culture period, cell culture supernatants are assayed for IL-1b, TNF-a, IL-6 and $PGE_2$ production using specific ELISA.

IL-1 mediated Cytokine Production

Human peripheral blood mononuclear cells are isolated from fresh human blood according to the procedure of Chin and Kostura, J. Immunol. 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh autologous human serum, penicillin streptomycin (10 U/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution. and are incubated for 24 hours. at 37° C. in 5% $C_{O2}$. At the end of the culture period, cell culture supernatants are assayed for TNF-a, IL-6 and $PGE_2$ synthesis using specific ELISA.

Determination of IL-1b, TNF-a, IL-6 and Prostanoid Production from LPS or IL-1 Stimulated PBMC's IL-1b ELISA Human IL-1b can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Maryland.) diluted in Dulbecco's phosphate-buffered saline (—$MgCl_2$,—$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1b standards are prepared from purified recombinant IL-1b produced from E. coli. The highest concentration begins at 10 ng/mL followed by 11 two-fold serial dilutions. For detection of IL-1b from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1b polyclonal antisera diluted 1:500 in PBS-Tween is added to the plate and incubated for 1 hour at room temperature followed by six washes with PBS-Tween. Detection of bound rabbit anti-IL-1b IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-a ELISA

Inmulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-a polyclonal serum purchased from Genzyme. All other operations are identical to those described above for IL-1b. The standards are prepared in PBS-Tween +10% FBS or HS. Eleven 2 fold dilutions are made beginning at 20 ng/mL TNF-a.

IL-6 ELISA

Levels of secreted human IL-6 are also determined by specific trapping ELISA as described previously in Chin and Kostura, J. Immunol. 151,5574–5585 (1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1b. The standards are prepared in PBS-Tween +10% FBS or HS. Eleven 2 fold dilutions are made beginning at 50 ng/mL IL-6.

$PGE_2$ production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wa) are maintained in culture medium supplemented with 15% fetal bovine serum and 1% CS-HBGF consisting of aFGF and heparin. The cells are then diluted 20-fold before being plated (250 µl) into gelatin coated 96-well plates. Prior to use, culture medium is replaced with fresh medium (200 µl). Buffer or test compound (25 µl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Min.). All data is presented as mean value (ng/mL) of multiple samples based on the standard curve. IC50 values where appropriate are generated by non-linear regression analysis.

What is claimed is:

1. A compound of the formula (I)

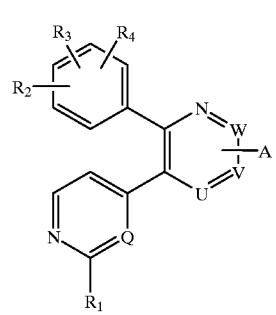

wherein
A is hydrogen, or a saturated heterocyclic group, linked via a carbon atom, selected from pyrrolidine, morpholine and piperidine; with the nitrogen atom or other ring atoms of said saturated heterocyclic group optionally substituted with hydrogen or $C_1$–$C_6$ alkyl;

Q[, U, V and W are independently] is CH or N;

U and V arc each CH;

W is N;

R¹ is hydrogen or NH(C₁–C₆ alkyl) aryl;

R², R³ and R⁴ independently represent a member selected from the group consisting of hydrogen, halo, hydroxy, CF₃, NH₂, NO₂, C₁–C₆ alkyl, 1–3 substiuent substituted C₁–C₆ alkyl, C₁–C₆ alkoxy, 1–3 substiuent substituted C₁–C₆ alkoxy, C₃–C₈ cycloalkyl, 1–3 substiuent substituted C₃–C₈ cycloalkyl, or aryl, wherein said substitents are each independently C₃–C₆cycloalkyl;

or a pharmaceutically acceptable addition salt and/or hydrate thereof, or where applicable, a geometric or optical isomer or racemic mixture thereof.

2. The compound according to claim 1 wherein

A is hydrogen, or piperidine with the nitrogen atom substituted with hydrogen or C₁–C₆ alkyl;

[Q, U and W are independently CH or N;]

R¹ is hydrogen or NHCH(CH₃) phenyl;

R², R³ and R⁴ are independently hydrogen or CF₃;

or a pharmaceutically acceptable addition salt and/or hydrate thereof, or where applicable, a geometric or optical isomer or racemic mixture thereof.

3. The compound according to claim 1 represented by one of the following structural formulas:

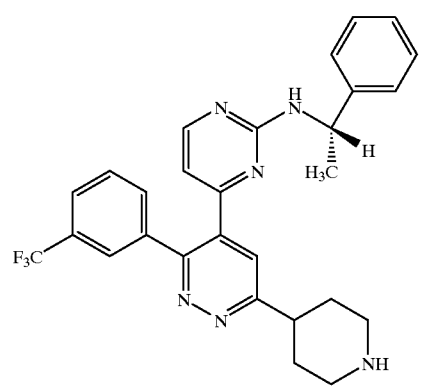

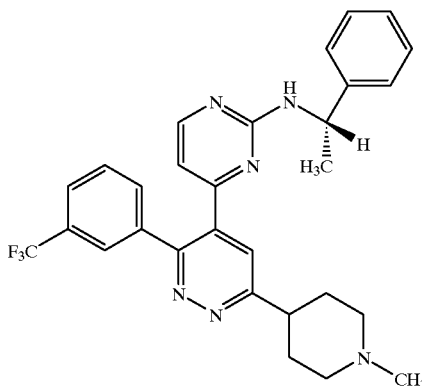

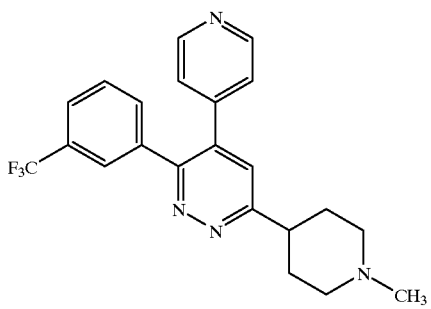

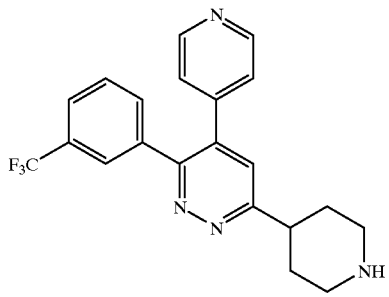

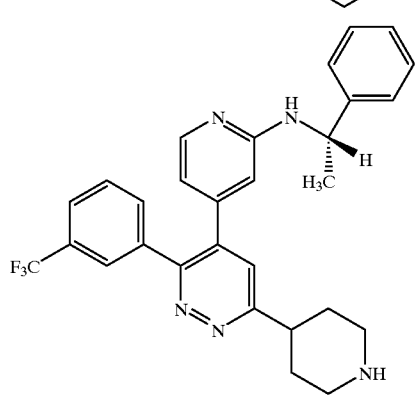

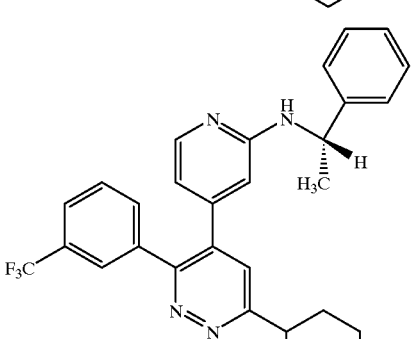

4. A pharmaceutical composition which is comprised of a compound in accordance with claim 1 in combination with a pharmaceutically acceptable carrier.

5. A pharmaceutical composition which is produced by combining a compound in accordance with claim 1 and a pharmaceutically acceptable carrier.

6. A process for making a pharmaceutical composition comprising combining a compound of claim 1 and a pharmaceutically acceptable carrier.

7. A compound represented by

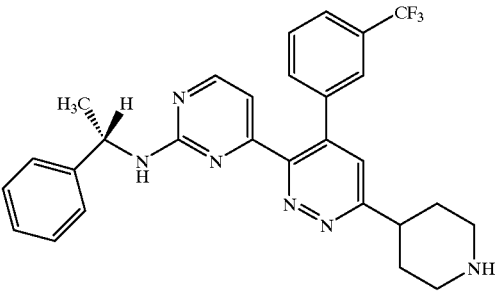

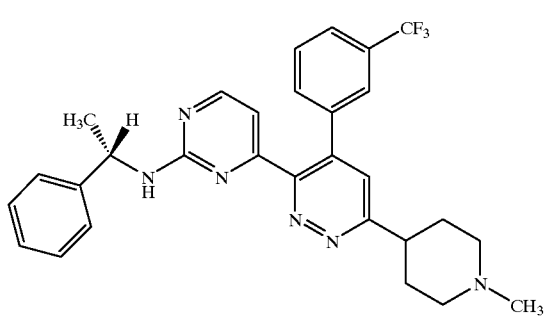
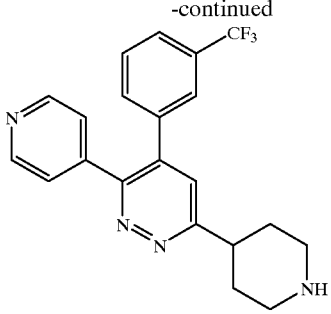
or a pharmaceutically acceptable salt thereof.
* * * * *